(12) United States Patent
Joplin

(10) Patent No.: US 10,189,643 B2
(45) Date of Patent: Jan. 29, 2019

(54) SYSTEMS AND METHODS FOR A CHECK / EXCEPTION STATION

(71) Applicant: Express Scripts Strategic Development, Inc., St. Louis, MO (US)

(72) Inventor: Jonathan W. Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 16/108,785

(22) Filed: Aug. 22, 2018

(65) Prior Publication Data

US 2018/0362254 A1    Dec. 20, 2018

Related U.S. Application Data

(63) Continuation of application No. 15/472,738, filed on Mar. 29, 2017, now Pat. No. 10,059,520, which is a continuation of application No. 14/803,009, filed on Jul. 17, 2015, now Pat. No. 9,639,668.

(60) Provisional application No. 62/028,211, filed on Jul. 23, 2014.

(51) Int. Cl.

| G06F 19/00 | (2018.01) |
|---|---|
| B25J 9/00 | (2006.01) |
| G16H 20/10 | (2018.01) |
| B65G 1/137 | (2006.01) |
| G06Q 10/08 | (2012.01) |
| B25J 11/00 | (2006.01) |
| G05B 15/02 | (2006.01) |
| G06Q 30/00 | (2012.01) |

(52) U.S. Cl.
CPC .......... B65G 1/1378 (2013.01); B25J 9/0093 (2013.01); B25J 11/00 (2013.01); B65G 1/1373 (2013.01); G05B 15/02 (2013.01); G06F 19/00 (2013.01); G06Q 10/0832 (2013.01); G16H 20/10 (2018.01); G06Q 30/018 (2013.01)

(58) Field of Classification Search
CPC ... B65G 1/1378; B25J 9/0093; G06F 19/3475
See application file for complete search history.

(56) References Cited

U.S. PATENT DOCUMENTS

| 5,771,657 A | 6/1998 | Lasher et al. |
|---|---|---|
| 6,176,392 B1 | 1/2001 | William |
| 6,892,512 B2 | 5/2005 | Rice et al. |
| RE40,510 E | 9/2008 | Lasher et al. |
| 7,765,776 B1 | 8/2010 | Leu et al. |

(Continued)

*Primary Examiner* — Thomas Randazzo
(74) *Attorney, Agent, or Firm* — Husch Blackwell LLP

(57) ABSTRACT

A system comprising a holding area, a manual section, a distribution section, and at least one conveyor. The manual section may include a handling area enabled for pill counting, pharmacist verification, exception handling, or combinations thereof. The distribution section may be disposed proximate the handling area and the manual section, and may include a robot and a scanner. The at least one conveyor may enable transportation of a container between said distribution section and said manual section. The robot may be adapted to pick a container from the holding area and move the container to the scanner for scanning. The robot may also be further adapted to place the container onto the conveyor to direct the container to a handling area which is enabled for an action based on the scan.

17 Claims, 8 Drawing Sheets

(56) References Cited

U.S. PATENT DOCUMENTS

| | | | |
|---|---|---|---|
| 7,853,355 B1 | 12/2010 | Willemse et al. | |
| 8,215,543 B2 * | 7/2012 | Carson | G07F 9/026 |
| | | | 235/375 |
| 8,406,917 B2 | 3/2013 | Khan et al. | |
| 8,571,700 B2 | 10/2013 | Keller et al. | |
| 8,861,816 B2 | 10/2014 | Lang et al. | |
| 9,122,783 B2 | 9/2015 | Carson et al. | |
| 9,394,107 B1 | 7/2016 | Eller et al. | |
| 9,639,668 B2 | 5/2017 | Joplin | |
| 2003/0125836 A1 | 7/2003 | Chirnomas | |
| 2005/0143857 A1 | 6/2005 | Chirnomas | |
| 2005/0171813 A1 | 8/2005 | Jordan | |
| 2006/0074521 A1 | 4/2006 | Rice et al. | |
| 2006/0090424 A1 * | 5/2006 | Tokarz | B65B 5/105 |
| | | | 53/448 |
| 2010/0089997 A1 * | 4/2010 | Carson | G07F 9/026 |
| | | | 235/375 |
| 2011/0282476 A1 | 11/2011 | Hegemier et al. | |
| 2011/0313567 A1 | 12/2011 | Willemse et al. | |
| 2012/0245728 A1 | 9/2012 | Koholka | |
| 2015/0120039 A1 * | 4/2015 | Nishibue | B65B 57/06 |
| | | | 700/230 |
| 2015/0128532 A1 | 5/2015 | Miller et al. | |

* cited by examiner

US 10,189,643 B2

SYSTEMS AND METHODS FOR A CHECK / EXCEPTION STATION

CROSS-REFERENCE TO RELATED APPLICATION

This application is a continuation of U.S. patent application Ser. No. 15/472,738, filed Mar. 29, 2017; said application is a continuation of U.S. patent application Ser. No. 14/803,009, filed on Jul. 17, 2015 and issued on May 2, 2017 as U.S. Pat. No. 9,639,668; said application claims priority to U.S. Provisional Patent Application No. 62/028,211, filed Jul. 23, 2014. The entire disclosures of U.S. application Ser. Nos. 15/472,738, 14/803,009, and U.S. Provisional Patent Application No. 62/028,211 are hereby incorporated herein by reference.

FIELD

The present application relates generally to the technical field of automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

DETAILED DESCRIPTION

Example systems and methods for operation of a check/exception station (e.g., in a pharmacy) are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other containers and packaging having a quantity of a prescription drug therein.

The prescription drugs may be dispensed at various sections of the high volume pharmacy. After dispending, some containers may be reviewed by a pharmacist for proper pill count, exception handling, prescription verification, and the like. As a non-limiting example, fulfilled prescriptions may be manually reviewed and/or verified by a pharmacist, as may be required by state or local law. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station.

Figure 1:
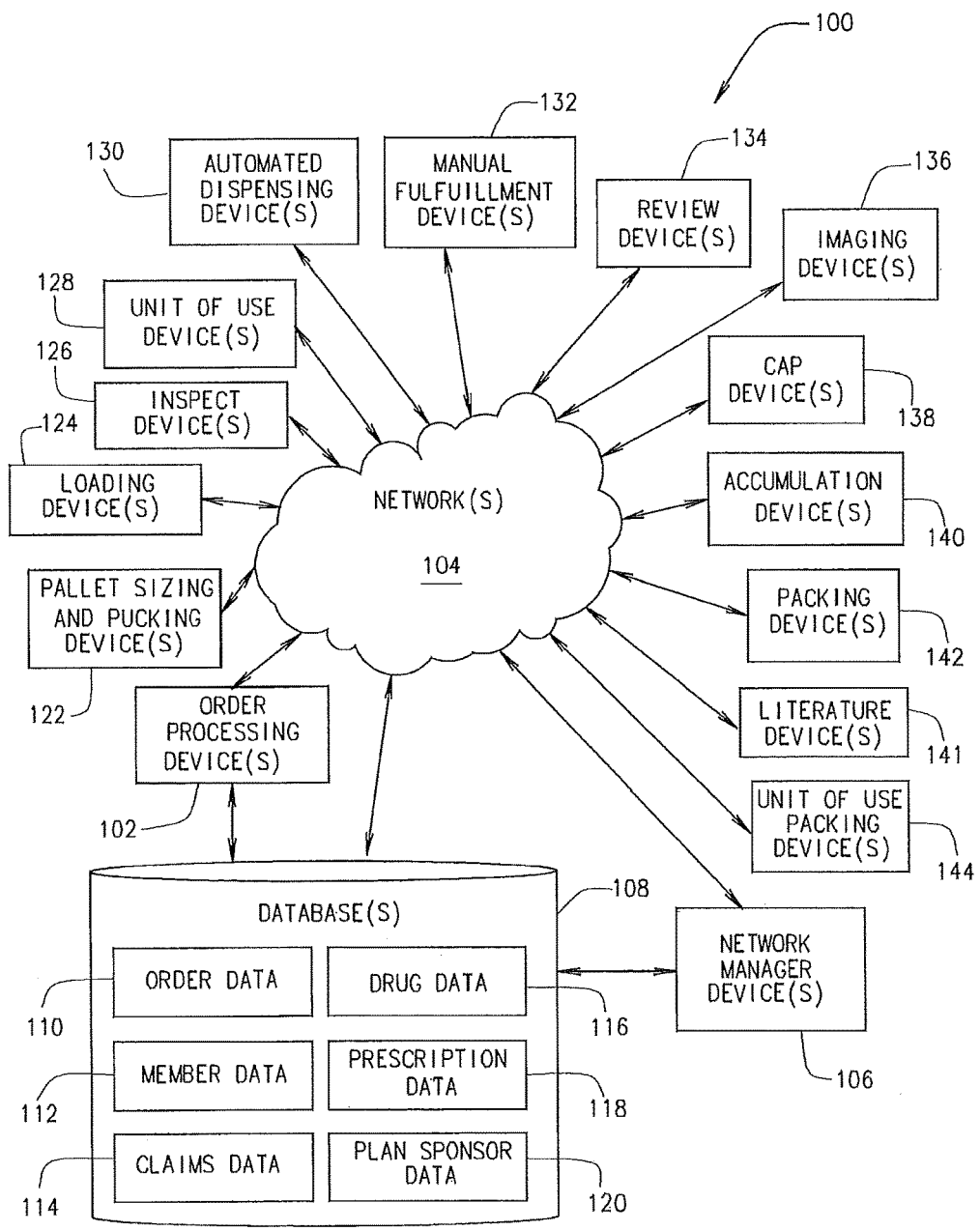
FIG. 1 is a block diagram of an example system, according to an example embodiment.

FIG. 1 is a block diagram of an example system 100, according to an example embodiment. While the system 100 is generally described as being deployed in a high volume pharmacy (e.g., a mail order pharmacy, a direct delivery pharmacy, an automated pharmacy, and the like), the system 100 may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together.

Examples of the devices 102, 106 include a set-top box (STB), a receiver card, a mobile telephone, a personal digital assistant (PDA), a display device, a portable gaming unit, a tablet, and a computing system; however other devices may also be used. For example, the devices 102, 106 may include a mobile electronic device, such an IPHONE or IPAD device by Apple, Inc., mobile electronic devices powered by ANDROID by Google, Inc., and a BLACKBERRY device by Blackberry Limited. The order processing device 102 may also include other computing devices, such as desktop computing devices, notebook computing devices, netbook computing devices, gaming devices, servers, and the like. The device 102 may include circuitry, a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software as a service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of container in which the drug is or is preferably dispensed. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet and during movement through the fulfillment process. Different pucks may have differently sized and shaped receptacles to accommodate containers of differing sizes, as may be appropriate for different prescriptions. Pucks allow the standardization of equipment engaging differently sized drug containers such that some automated equipment can move the drug container by gripping the puck that is supporting the container and allow the use of a standardized pallet that holds a plurality of pucks have a same outer dimension while having differently sized receptacles therein to hold differently sized drug containers. The pucks may also operate to ensure that a drug container is centered in a location on the pallet.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, a pick and place mechanism, or the like. In one embodiment, the loading device 108 has robotic arms or pickers to grasp a prescription container and move it to and from a pallet. The loading device 124 may also print a label which is appropriate for a container that is to be loaded onto the pallet, and apply the label to the container. The pallet may be located on a conveyor assembly during these operations. In an example embodiment, the drug containers may be positioned in the pucks by the loading device 124 prior to the pucks being placed in the pallet.

The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispensed by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100. In an example embodiment, the container may be joined with other containers in a prescription order for a patient or member, e.g., on a pallet or at the accumulation device 140. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise.

In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers, into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of containers to be bagged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g. by conveyors), networked, and/or otherwise in contact with one another or integrated with one another, e.g., at the high volume fulfillment center. In addition, the functionality of a device may be split among a number of discrete devices and/or combined with other devices.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

Figure 2:
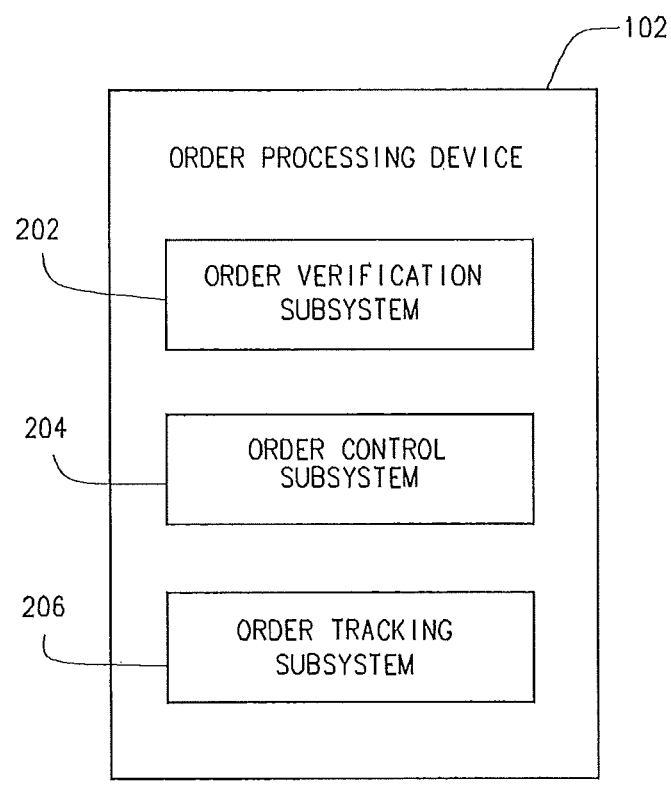
FIG. 2 is a block diagram of an example order processing device that may be deployed within the system of FIG. 1, according to an example embodiment.

FIG. 2 illustrates the order processing device 102, according to an example embodiment. The order processing device 102 may be used by one or more than one operator to generate prescription orders, make routing decisions, make prescription order consolidation decisions, track literature within the system 100, and/or view order status and other order related information. For example, the prescription order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100.

In some embodiments, the order control subsystem 204 may identify the prescribed drug in one or more than one prescription order as capable of being fulfilled by the automated dispensing device 130. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130.

In some embodiments, the order control subsystem 204 may identify the prescribed drug in one or more than one prescription order as needing to be fulfilled manually and may direct the container or order component to the manual fulfillment device 132 to achieve the manual fulfillment. The order control subsystem 204 may determine which prescriptions are to be launched, and may determine that a pallet of manual-fill containers is to be launched. The order control subsystem 204 may determine that a manual-fill prescription of a specific pharmaceutical is to be launched, and may examine a queue of orders awaiting fulfillment for other prescription orders which will be filled with the same pharmaceutical. The order control subsystem 204 may then launch orders with similar manual-fill pharmaceutical needs together in a pallet to the manual fulfillment device 132. As the devices 122-144 may be interconnected by a system of conveyors or other container movement systems, the order control subsystem 204 may control various conveyors to deliver the pallet from the loading device 124 to the manual fulfillment device 132, for example.

The order tracking subsystem 206 may track a prescription order as it progresses (or stops) toward fulfillment. The order tracking subsystem 206 may track, record and/or update order history, order status, or the like. The order tracking subsystem 206 may store data locally (e.g., in a memory) or as a portion of the order data 110 stored in the database 108.

Figure 3A:
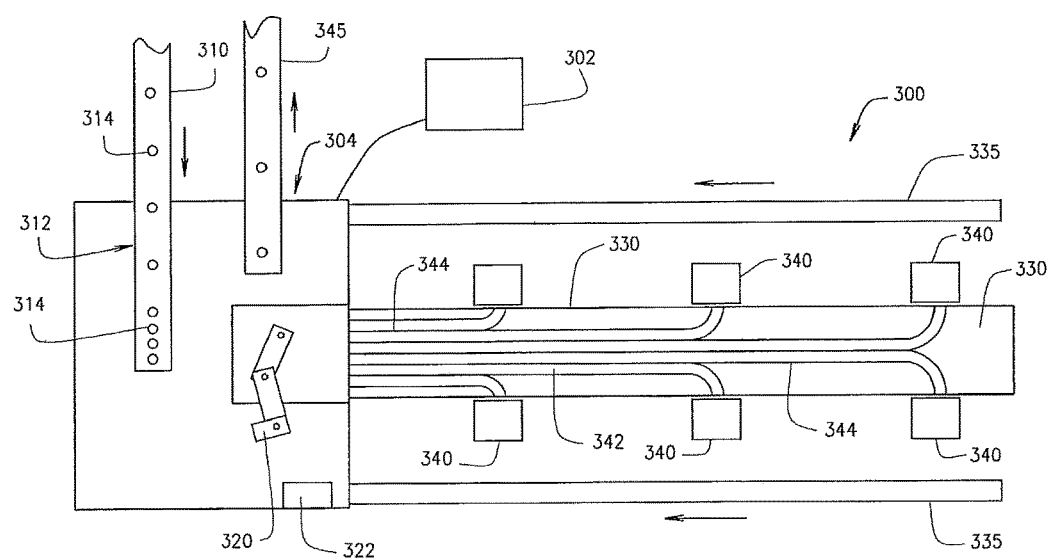
FIG. 3A is a schematic plan view of a check and exception center that may be deployed within the system of FIG. 1, according to an example embodiment.
Figure 3B:
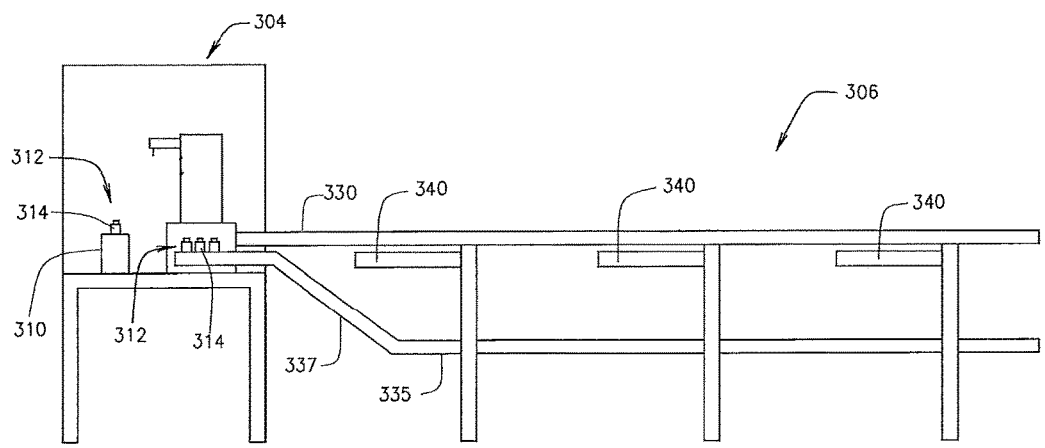
FIG. 3B is a schematic elevation view of the check and exception center that may be deployed within the system of FIG. 1, according to an example embodiment.

FIGS. 3A and 3B illustrate a check and exception center 300 according to an example embodiment. The review device 134 of FIG. 1 may be deployed in the system 100, or may be otherwise deployed. A check and exception center 300 may be deployed within a review device 134 of a pharmacy, and may be operated by one or more pharmacists to manually handle certain prescription containers, or otherwise implemented and/or used. Certain prescription drugs that have been filled in a container 314 may be checked by appropriate pharmacy personnel after filling but before packaging, for various reasons. The inspection could happen as a result of a specific event occurring. As non-limiting examples, a wrong pill color detection may be made by an imaging device, or a wrong weight detection may be made of the container 314, or a wrong pill depth may be identified in the container 314. Alternatively, the inspection could happen as a result of general operations, such as manually checking and verifying one container 314 out of a predetermined number of filled pill containers 314. The check and exception center 300 may more accurately and quickly process prescription containers 314 subject to check/exception. The center 300 may balance the workload among different pharmacy personnel, direct containers within the center 300 based on personnel expertise or anticipated amount of time to resolve current or previous container with an issue, etc., as discussed in detail below The check and exception center 300 may include a control unit 302 which may operate at the direction of the order processing device 102. The check and exception center 300 may also include a distribution section 304 automating distribution of containers 314 for pharmacist handling, and a manual area 306 in which a pharmacist may perform prescription verification and exception handling actions on a container 314. A container 314 may represent an order component of a prescription order. One or more than one order component may constitute a prescription order. The check and exception center 300 may also include a feed conveyor 310 may supply containers 314 to a holding area 312, which holds containers 314 awaiting action.

The distribution section 304 may include a robot 320 and a scanner 322. The robot 320 may be a SCARA robot or the like. In an example embodiment, a container 314 is picked by the robot 320 and distributed to the manual section 306. In some embodiments, the container 314 may be selected from other containers 314 as directed by the order processing device 102. A single container or multiple containers may be unloaded and distributed from the holding area 312. The robot 320 may be adapted to pick the container 314 from the holding area 312 and scan the container 314 via the scanner 322. The container 314 may be empty and/or uncapped, and/or may be filled and capped, or in any other state. The cap may be screwed or twisted onto the top of the container 314, pressed onto to the top of the container 314, or otherwise. The scanner 322 may include an image sensor that captures an image of the container 314 and label if available, and/or a barcode scanner. The robot 320 may be adapted to rotate the container 314 for the scanner 322 to obtain attributes, such as identifying data, from the label. Other devices may additionally or alternatively be used to remove the container 314 from the holding area 312, or the container 314 may be manually removed. In some embodiments, an escapement may be used, and the container 314 may be scanned while the container 314 is in the escapement. Thereby, the robot 320 may avoid rotating the container 314 in front of the scanner 322 to scan the container 314.

The distribution section 304 may further include a delivery conveyor 330 and a return conveyor 335. Delivery conveyor 330 may transport one or more than one container 314 from the robot 320 to a handling area 340. Return conveyor 335 may transport one or more than one container 314 from a handling area 340 to the robot 320. A single delivery conveyor 330 or multiple delivery conveyors 330 may be incorporated into the check and exception center 300. A single return conveyor 335 or multiple return conveyors 335 may be incorporated into the check and exception center 300. As shown, the return conveyor 335 may be positioned below the delivery conveyor 330, and may run in the opposite direction thereof. However, in some embodiments, the return conveyor 335 may be positioned alongside the delivery conveyor 330 or in other suitable locations. The delivery conveyor 330 and the return conveyor 335 may be straight, curved, or otherwise implemented according to the space available and location of the manual section 306.

The manual area 306 may include a handling area 340. One or multiple handling areas 340 may be included in a single manual section 306. For example, FIG. 3A depicts six handling areas 340 in a single manual section 306. The delivery conveyor 330 may deliver the containers 314 to the handling area 340. In some embodiments, the delivery conveyor 330 includes lanes 342 formed by guiderails 344. Each lane 342 may lead from the distribution section 304 to a specific handling area 340. Each lane 342 may be associated with its own delivery conveyor 330, or a single delivery conveyor 330 may be used for all lanes 342. The robot 320 may be controllable by the control unit 302 to pick the containers 314 and place them on the delivery conveyor 330 in the lane 342 leading to the handling area 340 selected by the control unit 302. A handling area 340 may be operated by a pharmacist for exception handling, sample counting, pharmacy verification, for other pharmacy-related operations, or the like.

The return conveyor 335 receives the containers 314 at the handling area 340 after handling by a pharmacist. As shown, return conveyor 335 may include an inclined section 337 which leads back to the robot 320 in the distribution section 304. The return conveyor 335 may include its own holding area 312, which may be a different holding area 312 from that used by the feed conveyor 310, or may be the same holding area 312. Once back in the holding area 312, a container 314 may again be selected by the robot 320, scanned, and again placed into a lane 342 as appropriate for additional action. In some embodiments, the container 314 may be placed on an outbound conveyor 345 by the robot 320. In some embodiments, the container 314 may be otherwise routed to the outbound conveyor 345.

Figure 4:
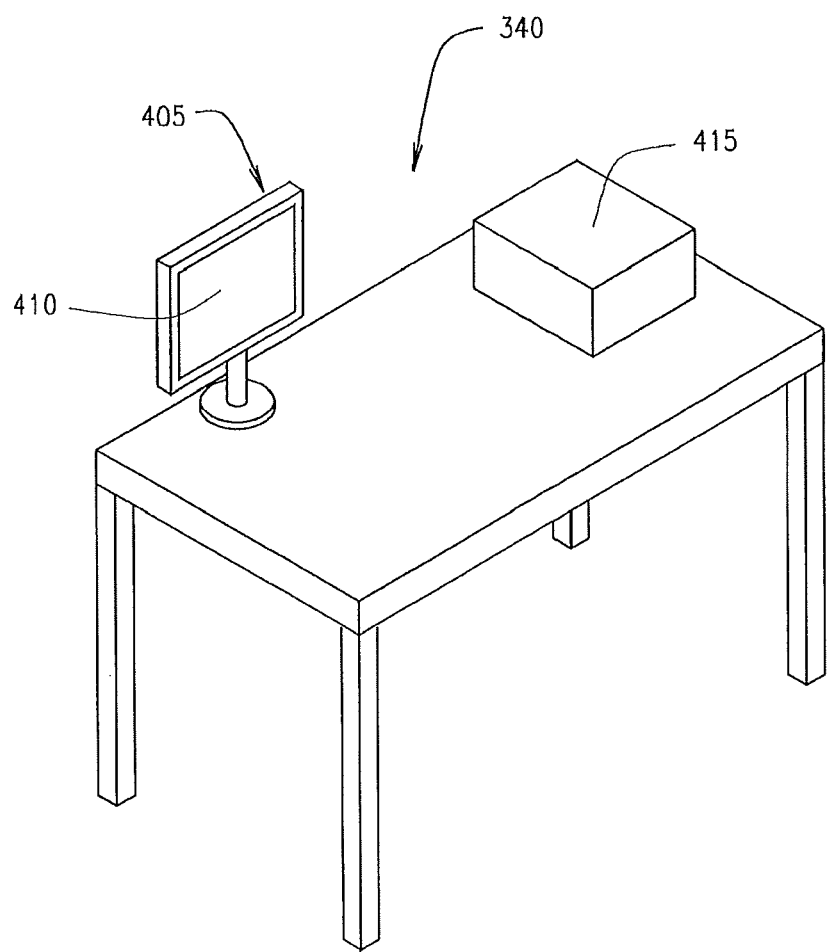
FIG. 4 is a schematic perspective view of a handling area of a check and exception center according to an example embodiment.

FIG. 4 illustrates a handling area 340, according to an example embodiment. Each handling area 340 may include an evaluation device 405. An evaluation device 405 may include a display 410. The display 410 may also be an input device, although other forms of input devices such as a mouse and/or keyboard and the like may also be used. The handling area 340 may include a pill counter 415 for verifying the count of pills from the container 314. In some embodiments, pill counter 415 may be a KIRBYLESTER® model KL15 pill counter or the like. A physician or technician may merely pour the contents of a container 314 into the pill counter 415, and the pill counter 415 verifies the number of pills which are in the container 314. The evaluation device 405 and/the or pill counter 415 may be in communication with the control unit 302. The evaluation device 405 may also enable a pharmacist or technical to utilize the handling area 340 to perform certain functions associated with the filling and distribution of prescription drugs to a patient. The evaluation device 405 may allow a pharmacist or technician to select a single or multiple actions to be taken at the handling area 340. In some embodiments, upon enabling a handling area 340 for use, a pharmacist may use the evaluation device 405 to initiate one or more than one action including exception handling, sample counting, pharmacy verification, and the like at the handling area 340. Additionally, once a container 314 is delivered to the handling area 340, the evaluation device 405 may inform the pharmacist to manually check the container 314 and its contents. The evaluation device 405 may inform the pharmacist or technician as to why the container 314 was sent to the handling area 340, and may instruct the pharmacist of the appropriate action to take. The evaluation device 405 may also display or otherwise provide verifying information, such as a copy of an electronic or paper prescription associated with the container 314, or information on a pharmaceutical which should be present in the container 314. The evaluation device 405 may further allow the pharmacist to make investigative actions, such as review photos of video of the filling of the container 314, obtain information regarding which lot the pharmaceutical came from or which machines touched the container 314, or the like. The pharmacist may also be able to confirm which actions were performed on the container 314. The handling area 340 is an example handling area that may be deployed in FIGS. 3A and 3B or otherwise.

Figure 5:
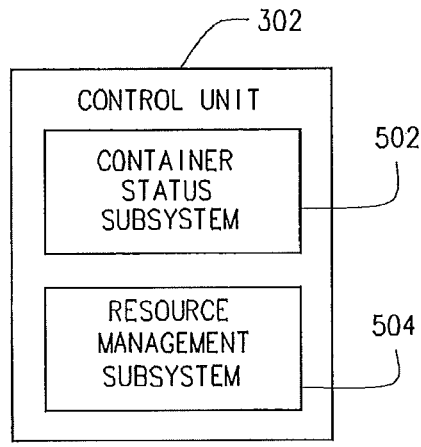
FIG. 5 is a block diagram of a control unit that may be deployed within the manual fill center of FIGS. 3A and 3B, according to an example embodiment.

FIG. 5 illustrates the control unit 302, according to an example embodiment. The control unit 302 may be deployed in the check and exception center 300, or may otherwise be deployed. The control unit 302 may be communicatively connected to one or more than one components in the distribution section 304 and/or the manual area 306, such as the robot 320, the evaluation device 405, and/or the pill counter 415. The control unit 302 may include a container status subsystem 502 and a resource management subsystem 504. The container status subsystem 502 may enable the control unit 302 to determine an action called for with respect to a container 314. The resource management subsystem 504 may enable the control unit 302 to monitor workloads assigned to various handling areas 340.

Figure 6:
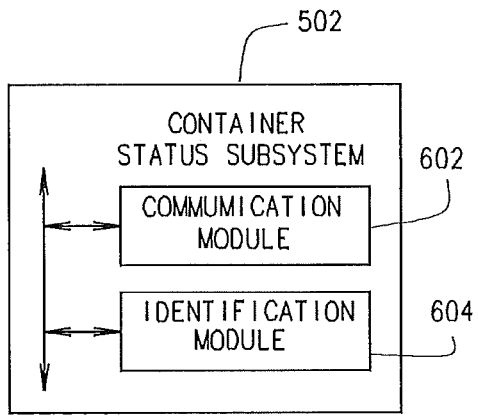
FIG. 6 is a block diagram of a container status subsystem that may be deployed within the control unit of FIG. 5, according to an example embodiment.

FIG. 6 illustrates an example container status subsystem 502 that may be deployed in the control unit 302, or may be otherwise deployed in another system. One or more modules are communicatively coupled and included in the container status subsystem 502 to enable the container status subsystem 502 to identify actions to be taken on a container 314. The modules of the container status subsystem 502 that may be included are a communication module 602 and/or an identification module 604. Other modules may also be included.

In some embodiments, the modules of the container status subsystem 502 may be distributed so that some of the modules are deployed in other devices within the pharmacy. In one embodiment, the modules are deployed in memory and executed by a processor coupled to the memory. The functionality contained within the modules 602, 604 may be combined into a lesser number of modules, further divided among a greater number of modules, or redistributed among existing modules. Other configurations including the functionality of the modules 602, 604 may be used.

The communication module 602 may manage communication from and/or within the check and exception center 300. For example, the communication module 602 may manage communications associated with the scanner 332 in order to identify the container 314 that has been picked by the robot 320. In some instances, the container 314 may have a label that is unreadable by the scanner 332, in which case the communication module 602 may flag the container 314 as an exception. Presuming the scanner 332 can read the label of container 314 and the container 314 can be identified, the identification module 604 may determine the type of action to be taken on the container 314. For example, one or more actions may be performed on the container 314, including but not limited to exception handling, pharmacy verification, and pill counting. The identification module 604 may be in communication with the order control subsystem 204 to make such determination, or such functionality may occur only in either the order control subsystem 204 or in identification module 604.

Figure 7:
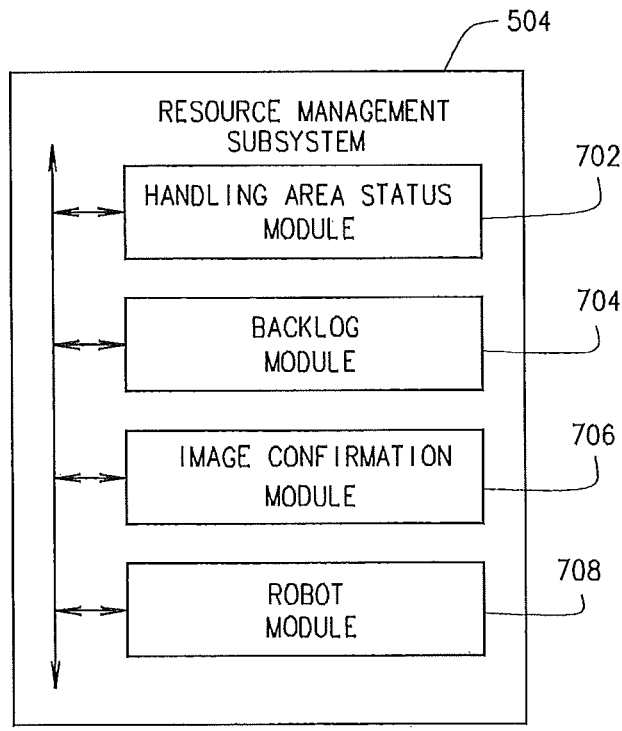
FIG. 7 is a block diagram of resource management subsystem that may be deployed within the control unit of FIG. 5, according to an example embodiment.

FIG. 7 illustrates an example resource management subsystem 504 that may be deployed in the control unit 302, or may be otherwise deployed in another system. One or more modules are communicatively coupled and included in the resource management subsystem 504. The modules of the resource management subsystem 504 that may be included are a handling area status module 702, a backlog module 704, an image confirmation module 706, and/or a robot module 708. Other modules may also be included.

In some embodiments, the modules of the resource management subsystem 504 may be distributed so that some of the modules are deployed in other devices within the pharmacy. In one embodiment, the modules are deployed in memory and executed by a processor coupled to the memory. The functionality contained within the modules 702-708 may be combined into a lesser number of modules, further divided among a greater number of modules, or redistributed among existing modules. Other configurations including the functionality of the modules 702-708 may be used.

The handling area module 702 may be in communication with evaluation device 405 at one or more than one of the handling areas 340. The handling area module 702 may receive information from the evaluation device 405 as to which handling areas 340 are presently manned by a pharmacist (or other person) and which are idle, and/or the type or types of actions currently being performed by the pharmacist at that handling area 340. When a handling area 340 is not manned by a pharmacist, the handling area module 702 may make a determination not to send the container 314 to that handling area 340.

The backlog module 704 may determine the currently workload of one or more than one of the handling areas 340. For example, if more than one handling area 340 is presently staffed by a pharmacist who is providing the action with respect to a given container 314, the backlog module 704 may determine the number of other containers 314 that are currently awaiting action at the relevant handling areas 340 so that the container 314 may be distributed to a handling area 340 with a lower workload.

When the container 314 is set to receive pharmacist verification, the image confirmation module 706 may access images taken within the pharmacy of the container 314 at one or more than one points during the pendency of the container 314. Such images may be transmitted to the evaluation device 405 at the appropriate handling area 340 for use by the pharmacist during the verification process.

The robot module 708 may operate the robot 320 to selectively pick the container 314 from the handling area 312. The robot module 708 may communicate with the handling area status module 702 and/or the backlog module 704, for example, in order to determine a lane 342 into which the container 314 is to be placed in order to queue the container 314 for action by a pharmacist at an appropriate handling area 340.

Figure 8:
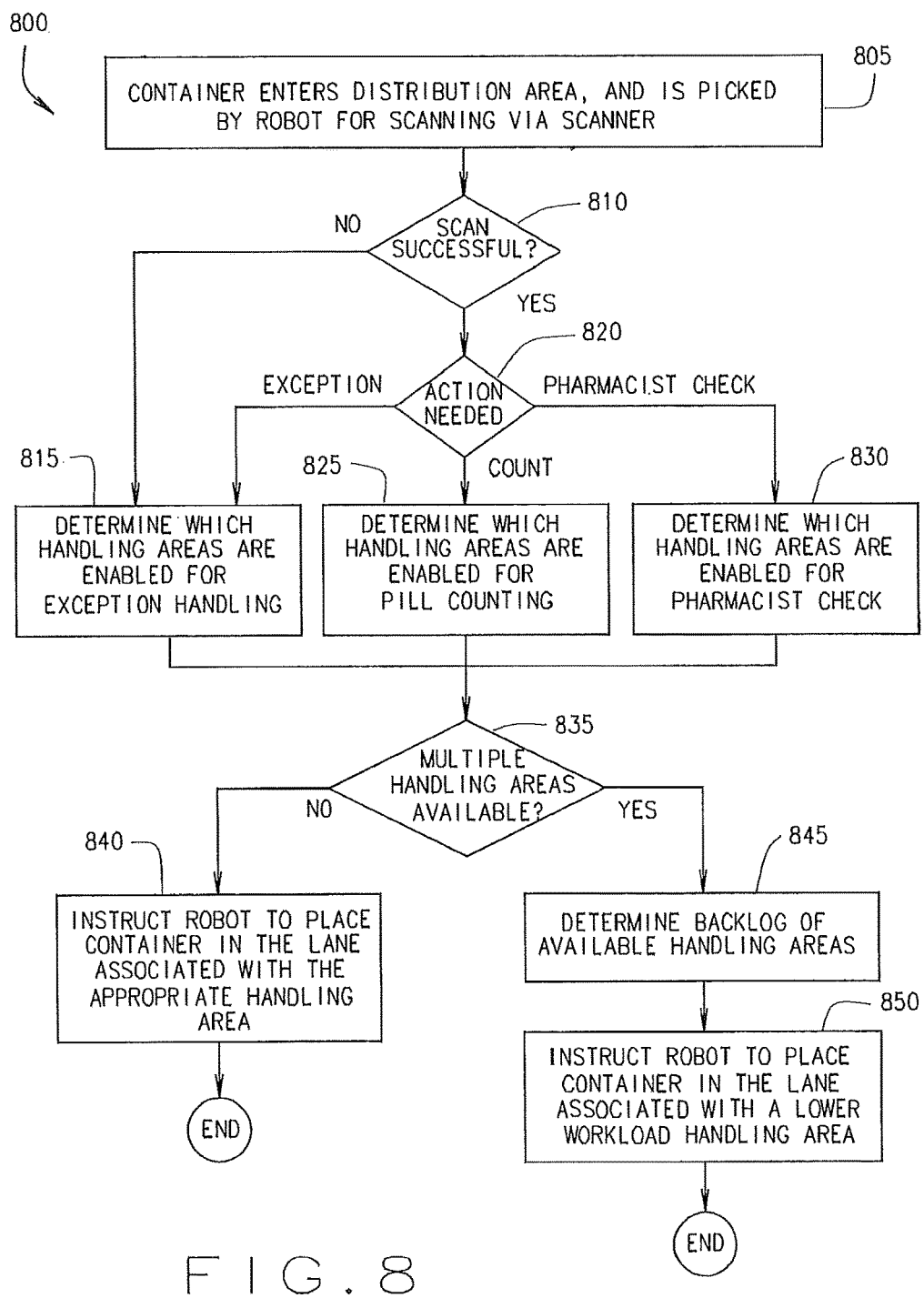
FIG. 8 is an example process flow illustrating a method of pharmacist checking, exception handling and pill counting, according to an example embodiment.

FIG. 8 illustrates a method 800 for checking and exception handling, according to an example embodiment. The method 800 may be performed in the check and exception center 300 as instructed by the control unit 302, or may be otherwise performed.

At block 805, as the container 314 enters the distribution area 304, the robot 320 may pick the container 314 and scan the label of the container 314 via the scanner 322. At decision point 810, a check may be made to determine if the scan was successful, or if the label could not be read. If the label could not be read, the container 314 may be deemed an exception and the method may advance to block 815, discussed in detail below. However, if the label is readable, the information obtained by the scanner 322 may then be sent to the communication module 602, and at block 815, the identification module 604 may determine the type of action needed by the container 314. If the container 314 is an exception, the method 800 advances to block 815 in which the handling area status module 702 may determine which of the handling areas 340 are enabled for exception handling. However, at decision point 820, if the contents of container 314 are to be counted, the method 800 advances to block 825 in which the handling area status module 702 may determine which of the handling areas 340 are enabled for pill counting. In some embodiments, at decision point 820, if the contents of container 314 are to be checked by a pharmacist, the method 800 advances to block 830 in which the handling area status module 702 may determine which of the handling areas 340 are enabled for pharmacist check.

The method 800 may advance to decision point 835 at which point a determination may be made as to whether one or more than one handling area 340 is appropriate. Where only a single handling area 340 is appropriate, at block 840, the robot module 708 may instruct robot 320 to place the container 314 into the lane 342 associated with that handling area 340.

However, it may be determined that more than one handling area 340 is associated with the type of action to be taken on the container 314 at block 835. For example, multiple pharmacists may be working on the relevant task at more than one handling area 340. At block 845, the resource management subsystem 504 may utilize the backlog module 704 to determine which handling area 340 will receive the container 314. At block 850, the robot module 708 instructs the robot 320 to place the container 314 into the selected lane 342 for delivery to the technician at the selected handling area 340.

Figure 9:
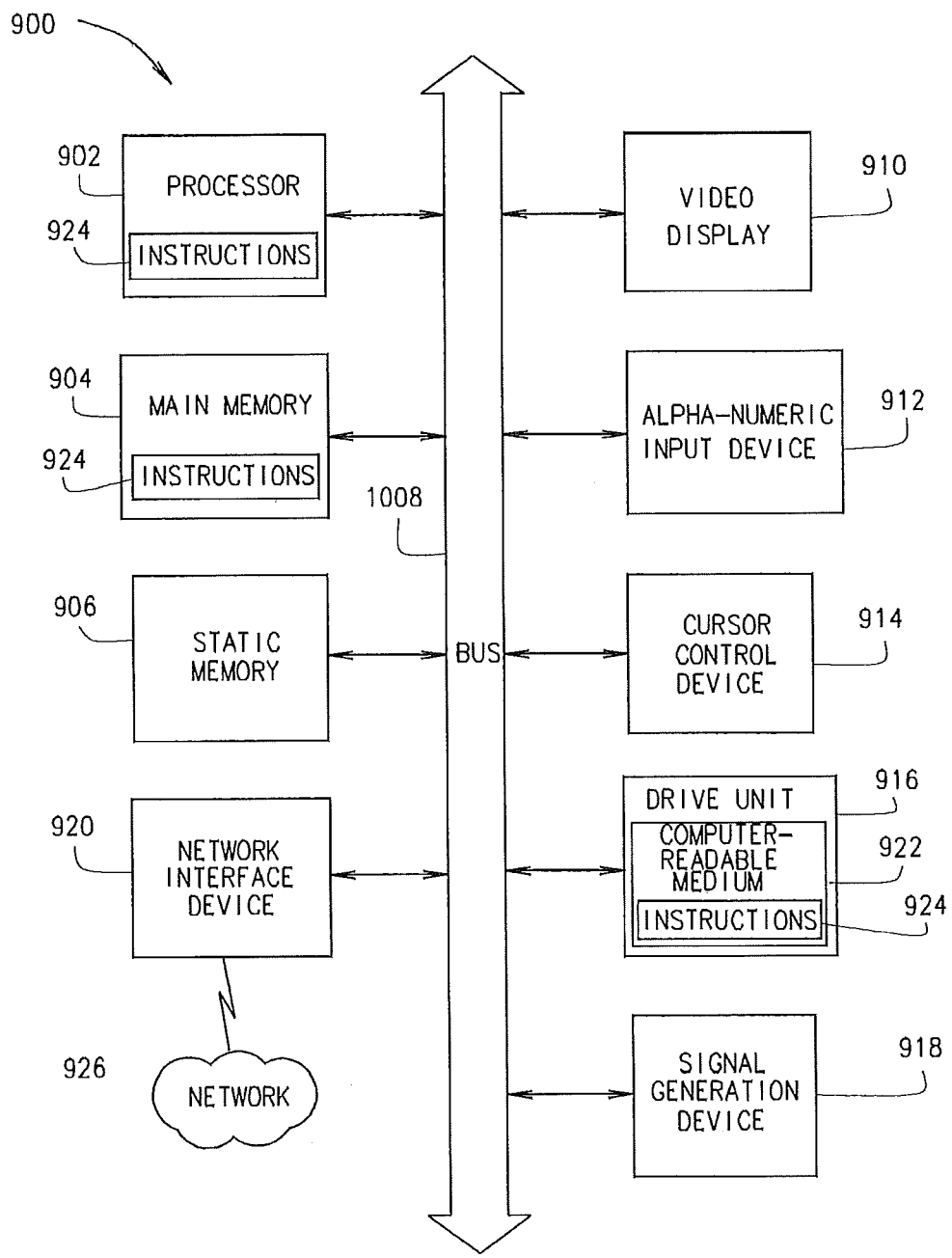
FIG. 9 is a block diagram of a machine in the example form of a computer system within which a set of instructions for causing the machine to perform any one or more of the methodologies discussed herein may be executed or stored.

FIG. 9 shows a block diagram of a machine in the example form of a computer system 900 within which a set of instructions may be executed causing the machine to perform any one or more of the methods, processes, operations, or methodologies discussed herein. The devices 102, 106, 122-144 may include the functionality of the one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a system is provided with a holding area, a distribution section and a manual section. The holding area is adapted to hold containers awaiting action. The distribution section is adjacent the holding section and has a robot adapted to select and pick containers from the holding section. The robot is disposed to distribute the container. The manual section is disposed adjacent the conveyor. The manual section is adapted for inspection of the container.

The present disclosure makes reference to a robot and words of similar import. A robot can be a machine capable of carrying out a complex series of actions automatically. These complex series of actions may include picking up, orientating, positioning and/or releasing a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, e.g., a robot may move location, have an articulated arm, have grasping structures that replicate like fingers and do not damage containers, and the like.

Thus, methods and systems for operation of a check/exception station have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A system comprising:
   a feed conveyor to supply a plurality of containers to a holding area;
   a robot to pick a container among the plurality of containers within the holding area and to distribute the picked container to a manual section including a plurality of handling areas;

a delivery conveyor to transport the picked container from the robot to a handling area among the plurality of handling areas; and a return conveyor to transport the picked container from the handling area back towards the robot.

2. The system of claim 1, wherein the delivery conveyor includes a plurality of lanes respectively formed by a plurality of guiderails.

3. The system of claim 2, further comprising:

a control unit communicatively coupled with the feed conveyor and the robot to select the handling area from among the plurality of handling areas; and an order processing device communicatively coupled with the control unit to select the picked container from among the plurality of containers, wherein the robot is controlled by the control unit and picks the picked container based on selection of the picked container by the order processing device, and wherein the robot places the picked container on the delivery conveyor in a lane among the plurality of lanes, the lane leading to the handling area selected by the control unit.

4. The system of claim 3, further comprising:

a scanner to scan the picked container, wherein the control unit is further communicatively coupled with scanner.

5. The system of claim 4, wherein the scanner includes an image sensor to capture an image of the picked container and a label affixed to the picked container.

6. The system of claim 4, wherein the robot is configured to rotate the picked container for scanning by the scanner.

7. The system of claim 2, wherein the delivery conveyor includes a single delivery conveyor for container transportation with the plurality of lanes.

8. The system of claim 2, wherein the delivery conveyors includes a plurality of delivery conveyors each for container transportation with a respective lane of the plurality of lanes.

9. The system of claim 1, further comprising:

an outbound conveyor to receive the picked container from the robot and transport the picked container to a different pharmacy area, wherein the robot is configured to pick the picked container and place the picked container in the outbound conveyor after the picked container is returned by the return conveyor from the handling area.

10. The system of claim 1, wherein the return conveyor is positioned below the delivery conveyor and runs in the opposite direction of the delivery conveyor.

11. The system of claim 1, wherein the picked container contains prescription drug therein and includes a cap.

12. The system of claim 1, wherein the picked container is uncapped and empty.

13. The system of claim 1, wherein the return conveyor includes an inclined section leading back to the robot.

14. The system of claim 1, where the container is a prescription drug bottle.

15. A method comprising:

supplying, through a feed conveyor, a plurality of containers to a holding area;

picking, with a robot, a container among the plurality of containers within the holding area;

distributing the picked container to a manual section including a plurality of handling areas;

transporting the picked container from the robot to a handling area among the plurality of handling areas using a delivery conveyor; and transporting the picked container from the handling area back towards the robot using a return conveyor.

16. The method of claim 15, further comprising:

picking the picked container and placing the picked container, using the robot, in an outbound conveyor after the picked container is returned by the return conveyor from the handling area; and transporting the picked container to a different pharmacy area using the outbound conveyor.

17. The method of claim 15, further comprising:

evaluating the picked container while the picked container is associated the handling area.

* * * * *